United States Patent
Barry et al.

(10) Patent No.: US 8,133,171 B2
(45) Date of Patent: Mar. 13, 2012

(54) WIRE SPRING GUIDE FOR FLEXIBLE ENDOSCOPE

(75) Inventors: James P. Barry, Charlton, MA (US); David Payeur, Southbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1270 days.

(21) Appl. No.: 10/452,301

(22) Filed: Jun. 2, 2003

(65) Prior Publication Data

US 2004/0242966 A1 Dec. 2, 2004

(51) Int. Cl.
*A61B 1/00* (2006.01)

(52) U.S. Cl. ........ 600/151; 600/139; 600/143; 600/146; 600/150

(58) Field of Classification Search .......... 600/146–151, 600/139–143
See application file for complete search history.

(56) References Cited

U.S. PATENT DOCUMENTS

| | | | | |
|---|---|---|---|---|
| 4,601,283 A * | 7/1986 | Chikama | ....................... | 600/151 |
| 4,753,223 A * | 6/1988 | Bremer | ....................... | 600/140 |
| 4,790,624 A * | 12/1988 | Van Hoye et al. | ............ | 385/118 |
| 4,846,573 A * | 7/1989 | Taylor et al. | ................ | 356/241.4 |
| 4,944,727 A * | 7/1990 | McCoy | .......................... | 604/528 |
| 5,531,664 A * | 7/1996 | Adachi et al. | .................. | 600/149 |
| 5,683,348 A * | 11/1997 | Diener | ........................... | 600/143 |
| 5,810,717 A * | 9/1998 | Maeda et al. | .................. | 600/151 |
| 5,860,914 A * | 1/1999 | Chiba et al. | .................... | 600/151 |
| 5,938,588 A | 8/1999 | Grabover et al. | ............. | 600/150 |
| 6,171,249 B1 | 1/2001 | Chin et al. | .................... | 600/461 |
| 6,179,776 B1 | 1/2001 | Adams et al. | .................. | 600/121 |
| 6,198,974 B1 * | 3/2001 | Webster, Jr. | .................. | 607/122 |
| 6,485,411 B1 * | 11/2002 | Konstorum et al. | .......... | 600/139 |

* cited by examiner

*Primary Examiner* — Matthew J Kasztejna

(74) *Attorney, Agent, or Firm* — St. Onge Steward Johnston & Reens LLC

(57) ABSTRACT

A medical device having a flexible shaft is provided, the flexible shaft including an active deflection section. The medical device also includes at least one control wire passing through at least a portion of the flexible shaft such that actuation of the at least one control wire causes deflection of the active deflection section of the flexible shaft. At least one control wire guide is provided which surrounds the at least one control wire along at least a portion of a length thereof. The at least one control wire guide is formed from a superelastic metal alloy and is configured as a helical spring.

26 Claims, 3 Drawing Sheets

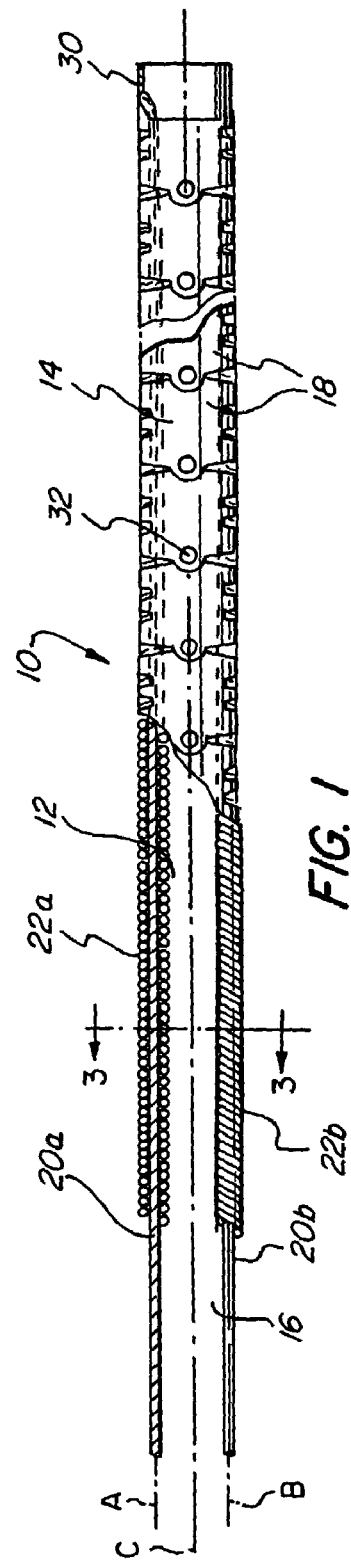
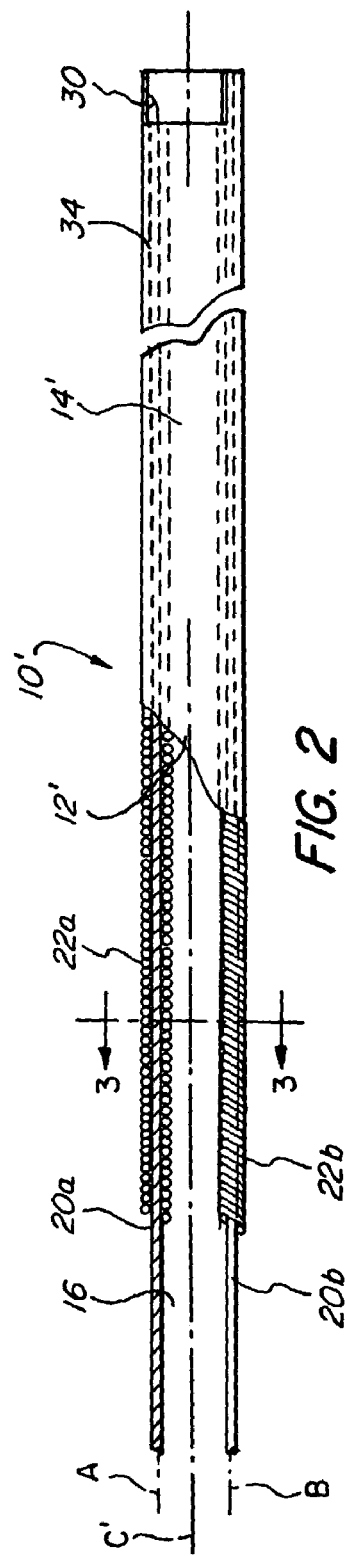

US 8,133,171 B2

WIRE SPRING GUIDE FOR FLEXIBLE ENDOSCOPE

FIELD OF THE INVENTION

The present invention relates generally to flexible medical devices, and more particularly to flexible-type endoscopic devices which employ one or more control wires for controlling the flexing or deflection of at least a portion of the devices.

BACKGROUND OF THE INVENTION

Generally, an endoscope is a medical device for insertion into a body passageway or cavity that enables an operator, positioned at a remote external location, to view and/or perform certain surgical procedures at a site internal to the patient's body. As is known, endoscopes may be either rigid or flexible, the later type providing either active or passive deflection of at least a portion thereof to facilitate reaching the internal site of interest. In general, a flexible endoscope includes a long flexible tubular member equipped with, for example, a miniature viewing device, an illumination device, and/or one or more working channels. The endoscope has a proximal end that remains external to the patient and a distal end having an endoscope tip for insertion into a body cavity of the patient.

Passive flexible endoscopes simply allow for the tubular member to deflect as it is inserted into various portions of the body (typically following the pathway of an elongated organ or cavity. Active flexible endoscopes on the other hand, allow the user to manipulate controls (typically at the proximal end of the endoscope) to cause at least a portion of the endoscope (typically the distal end) to deflect or flex in one or more directions. It is these active-type flexible endoscopes with which the present invention is most concerned.

A typical flexible endoscope 110 is illustrated in FIG. 8. An illumination device of endoscope 110 typically includes a lens 112 at an endoscope tip 114. Lens 112 is positioned proximate to a viewing device 116. Light emanates from lens 114 to enable viewing device 116 to capture images in the body cavity and electrically or optically transmit the images through a tubular body 118 of endoscope 110 for display at an external monitor. Once viewing the transmitted images, the endoscope operator may insert one or more surgical instruments through one or more working channels 120 to perform an endoscopic procedure at the internal body cavity site. These endoscopic procedures may include, for example, snare resections, injections, or biopsies of particular internal areas of the patient's body. Alternately, endoscope 110 may be used simply for viewing.

If flexible endoscope 110 is of the active type, at least one control wire 122 extending from a deflection control located at the proximal end to a distal end may be embedded within tubular body 118. Control wire 122 may be provided with a guide along at least a portion thereof in order to (1) keep the control wire 122 in place and prevent chaffing thereof by contact with other components within tubular body 118, and (2) provide a compression member inside tubular body 118 which prevents collapse of the shaft when control wire stress is applied.

In certain known devices, the wire guide comprises a coiled stainless steel wire to form a flexible tube around each control wire. A problem exists with these stainless steel coil wire guides in that the coil shape can expand during compression. This can result in a loss of deflection at the active deflection section of the endoscope. Another problem with such stainless steel coil wire guides is that they do not generally add significant stiffness and/or column strength to the endoscope shaft, do not reduce loss of deflection over time, and do not improve endoscope shaft rigidity for facilitated patient introduction.

In other prior art devices, continuous-walled tubes are used as the guides for the control wires. In traditional designs, these continuous-walled tubes are formed from stainless steel. More recent designs, such as those disclosed in U.S. Pat. No. 5,938,588, have formed such continuous-walled tubes from shape memory alloy materials. However, designs incorporating such continuous-walled tubes are only used effectively in applications which have a large bend radius. This is true because continuous-walled tubes can kink very easily, have no resilience (in the case of stainless steel tubes) or limited resilience (in the case of shape memory alloy materials), and can fatigue and permanently deform, thereby shortening the working life of the endoscope.

What is desired, therefore, is a control wire guide for use in a flexible endoscope the use of which does not result in a loss of deflection at the active deflection section of the endoscope, which adds stiffness and/or column strength to the endoscope shaft, which causes a reduction in loss of deflection over time as compared to known designs, which improves endoscope shaft rigidity for facilitated patient introduction, which can be used effectively in applications which have a small bend radius, which does not kink very easily, which has high resilience, and which does not fatigue and permanently deform, thereby shortening the working life of the endoscope.

SUMMARY OF THE INVENTION

Accordingly, it is an object of the present invention to provide a control wire guide for use in a flexible endoscope the use of which does not result in a loss of deflection at the active deflection section of the endoscope.

Another object of the present invention is to provide a control wire guide having the above characteristics and which adds stiffness and/or column strength to the endoscope shaft.

A further object of the present invention is to provide a control wire guide having the above characteristics and which causes a reduction in loss of deflection over time as compared to known designs.

Still another object of the present invention is to provide a control wire guide having the above characteristics and which improves endoscope shaft rigidity for facilitated patient introduction.

Yet a further object of the present invention is to provide a control wire guide having the above characteristics and which can be used effectively in applications which have a small bend radius.

Still a further object of the present invention is to provide a control wire guide having the above characteristics and which does not kink very easily.

Still yet another object of the present invention is to provide a control wire guide having the above characteristics and which exhibit high resilience.

Still yet another object of the present invention is to provide a control wire guide having the above characteristics and which does not fatigue and permanently deform, thereby shortening the working life of the endoscope.

These and other objects of the present invention are achieved by provision of a medical device having a flexible shaft, the flexible shaft including an active deflection section. The medical device also includes at least one control wire passing through at least a portion of the flexible shaft such that actuation of the at least one control wire causes deflection of the active deflection section of the flexible shaft. At least one control wire guide is provided which surrounds the at least one control wire along at least a portion of a length thereof. The at least one control wire guide is formed from a superelastic metal alloy and is configured as a helical spring.

In some embodiments, the at least one control wire guide is configured as a generally round spring formed from a coiled piece of material having a generally circular cross-section. In other embodiments, the at least one control wire guide is configured as a generally flat wire spring formed from a coiled piece of material having a generally rectangular cross-section. In certain embodiments, the superelastic metal alloy from which the at least one control wire guide is formed exhibits both shape memory and superelasticity properties. In certain of these embodiments, the superelastic metal alloy from which the at least one control wire guide is formed comprises a nickel-titanium alloy.

In some embodiments, the least one control wire comprises two control wires and the at least one control wire guide comprises two control wire guides. In some embodiments, the flexible shaft is generally round in cross-section. In certain embodiments, the active deflection section of the flexible shaft comprises a plurality of vertebrae pivotably connected together, while in other embodiments, the active deflection section of the flexible shaft comprises a generally continuous and flexible tubular body.

In some embodiments, the flexible shaft further comprises a passive deflection section. The flexible shaft may further comprise an elastomeric core through which the at least one control wire guide extends and/or may further comprise an outer flexible casing. In some embodiments, the medical device further comprises a fiber optic image bundle passing through the flexible shaft, a fiber optic illumination bundle passing through the flexible shaft and/or a working channel passing through said flexible shaft. In certain embodiments, the medical device comprises an endoscope.

In another aspect, the present invention is directed to an endoscope which includes a flexible shaft, the flexible shaft including an active deflection section formed from a plurality of vertebrae pivotably connected together. Two control wires pass through at least a portion of the flexible shaft, such that actuation of the control wires causes deflection of the active deflection section of the flexible shaft. A control wire guide surrounds each of the control wires along at least a portion of a length thereof. The control wire guides are formed from a superelastic metal alloy which exhibits both shape memory and superelasticity properties and are configured as helical springs.

In some embodiments, the control wire guides are configured as generally round springs formed from coiled pieces of material having a generally circular cross-section. In other embodiments, the control wire guides are configured as generally flat wire springs formed from coiled pieces of material having a generally rectangular cross-section. In certain embodiments, the superelastic metal alloy from which the control wire guides are formed comprises a nickel-titanium alloy.

In some embodiments, the flexible shaft is generally round in cross-section. The flexible shaft may further comprise a passive deflection section. In certain embodiments, the flexible shaft may further comprise an elastomeric core through which the control wire guides extend and/or may further comprise an outer flexible casing. In some embodiments, the endoscope further comprises a fiber optic image bundle passing through the flexible shaft, a fiber optic illumination bundle passing through the flexible shaft and/or a working channel passing through said flexible shaft.

The invention and its particular features and advantages will become more apparent from the following detailed description considered with reference to the accompanying drawings.

BRIEF DESCRIPTION OF THE DRAWINGS

FIG. 1 is a partially cross-sectional side view of an embodiment of a flexible endoscope incorporating a control wire guide in accordance with the present invention;

FIG. 2 is a partially cross-sectional side view of another embodiment of a flexible endoscope incorporating the control wire guide of FIG. 1;

DETAILED DESCRIPTION OF EMBODIMENTS OF THE INVENTION

Figure 3:
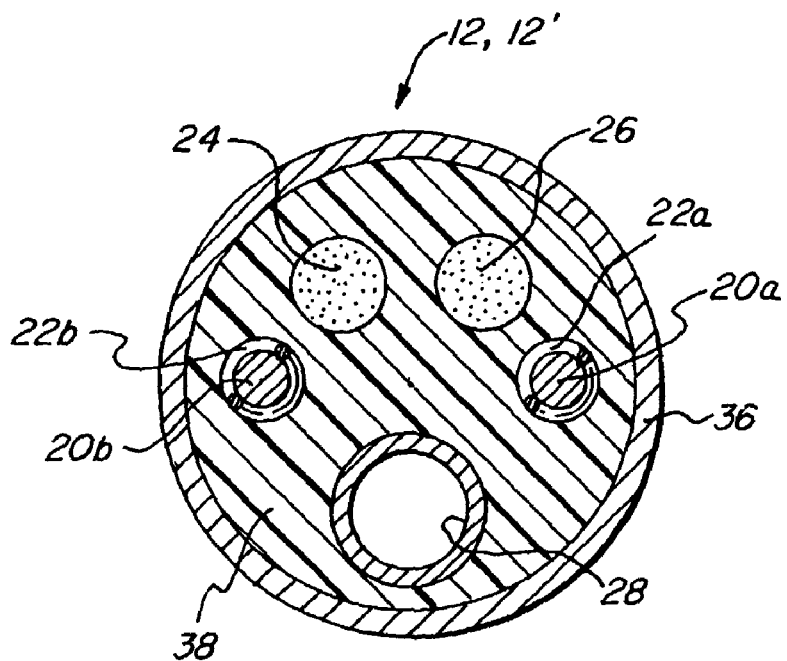
FIG. 3 is an enlarged cross-sectional view of an endoscope taken along line 3-3 of FIG. 1 or FIG. 2.
Figure 4:
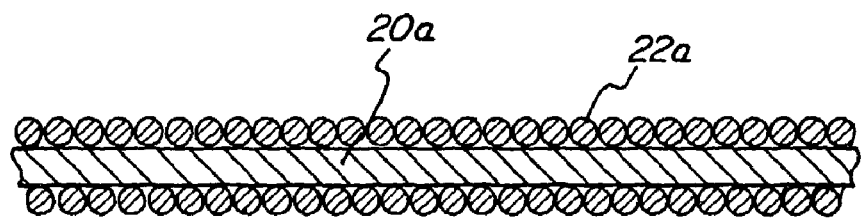
FIG. 4 is an enlarged cross-sectional view of an embodiment of the control wire guide of FIG. 1 or FIG. 2.
Figure 5:
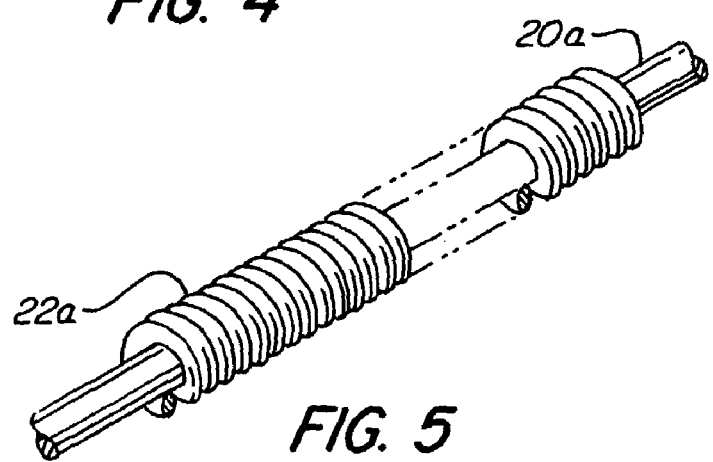
FIG. 5 is an isometric view of the embodiment of the control wire guide of FIG. 4.
Figure 6:
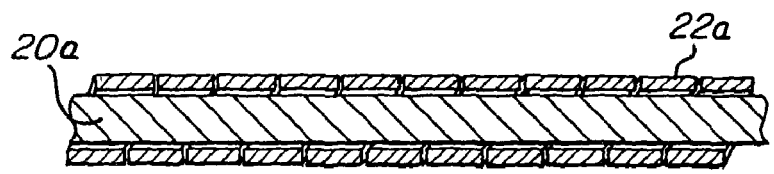
FIG. 6 is an enlarged cross-sectional view of another embodiment of the control wire guide of FIG. 1 or FIG. 2.
Figure 7:
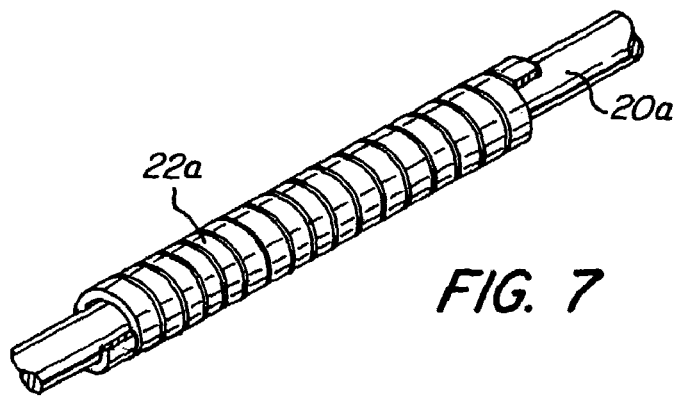
FIG. 7 is an isometric view of the embodiment of the control wire guide of FIG. 6.
Figure 8:
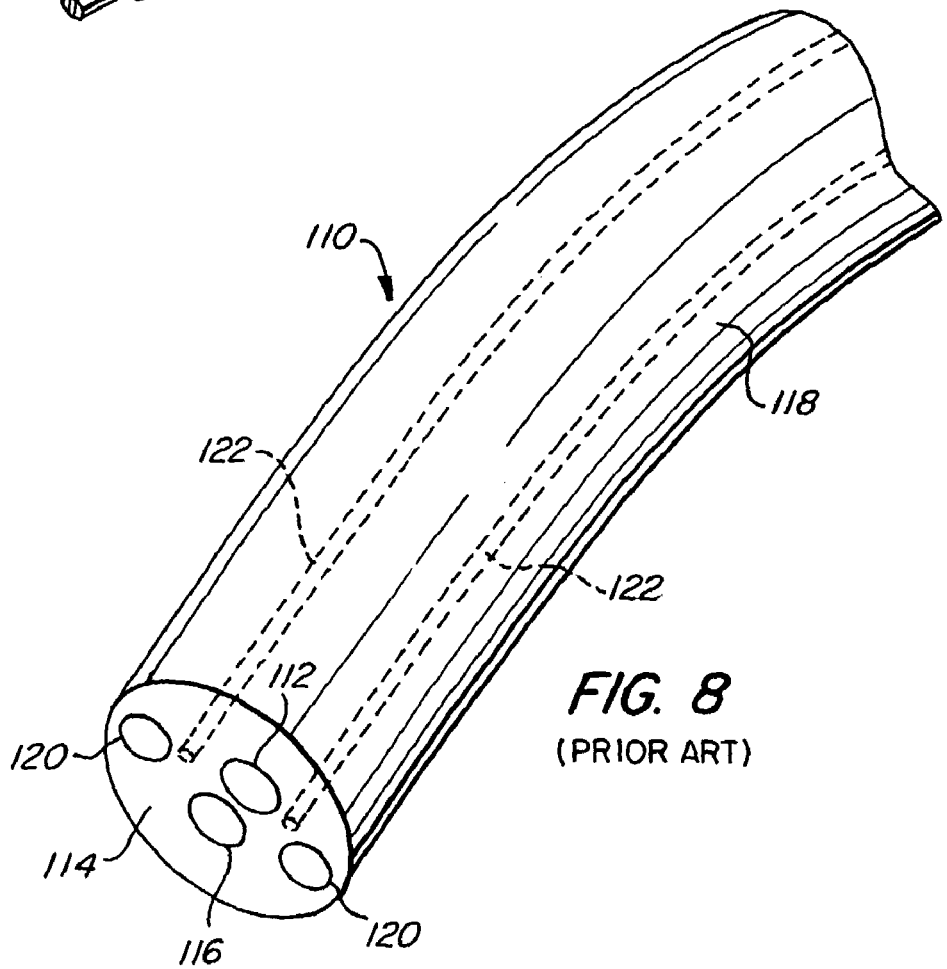
FIG. 8 is an isometric view, partially in phantom, of a prior art flexible endoscope.

Referring first to FIGS. 1 and 2, an endoscope 10, 10' incorporating features of the present invention is shown. Although, the present invention will be described with reference to the embodiments shown in the drawings, it should be understood that features of the present invention can be embodied in various different forms of alternate embodiments. Features of the present invention can be embodied in various different types of endoscopes or other medical devices. In addition, any suitable size, shape or type of elements or materials could be used.

Endoscope 10, 10' generally comprises a handle (not shown), a flexible shaft 12, 12' connected to the handle, and an active deflection section 14, 14' forming the distal end of the shaft 12, 12'. The flexible shaft 12, 12' may or may not include a passive deflection section 16 adjoining the active deflection section 14, 14'. In the embodiment shown in FIG. 1, active deflection section 14 comprises a plurality of articulating vertebrae 18, while in the embodiment shown in FIG. 2, active deflection section 14' generally comprises an extension of passive deflection section 16 which is provided with a control system as described below in order to cause active flexing or deflection thereof. As both types of active deflection schemes are well known in the art, further details are provided below only to the extent necessary to fully describe the features of the present invention.

A control system to control the active deflection section 14, 14' extends from the handle (not shown) to the active deflection section 14, 14' as shown in FIGS. 1 and 2. Referring now to FIG. 3 as well an FIGS. 1 and 2, the control system generally comprises a pair of control wires 20a, 20b, two control wire guides 22a, 22b, and an actuator (not shown) mounted on or near the handle. The control wires 20a, 20b are connected to the actuator at one end and are connected to the active deflection section 14, 14' at a second end.

Numerous configurations for the handle and the actuator are known in the art and do not form a part of the novelty of the invention. As such, although a small number of exemplary configurations are given below, these components are not shown in the Figures and it should be understood by those skilled in the art that any known, or later developed, handle and actuator configuration may be employed.

In one known design, the handle has a user operated slide or lever. The lever is connected to the actuator, and the actuator is adapted to pull and release the two control wires 20a, 20b of the control system. When the lever is moved by the user, the actuator is moved. The actuator may be a drum or pulley rotatably connected to the handle to pull one control wire 20a, 20b while releasing the other. In other exemplary designs, the actuator may be of any other type, such as a rocker arm, adapted to pull and release the control wires 20a, 20b of the control system. In still other exemplary designs, where the control system may have two or more pairs of control wires, the handle may have additional actuators and corresponding controls to drive the additional pairs of control wires. In yet other exemplary designs, the handle may have knobs or other suitable user operated controls for the control system. Numerous other designs are also possible.

Referring now specifically to FIG. 3, the flexible shaft 12, 12' is shown as being generally round in cross-section, although it is contemplated that it may have any of numerous other shapes. In one embodiment, the shaft 12, 12' has a 7.5 Fr diameter. In other embodiments, the flexible shaft 12, 12' could have any other suitable diameter. The flexible shaft 12, 12' includes the control wires 20a, 20b of the control system which are surrounded by control wire guides 22a, 22b along at least a portion thereof. In certain embodiments, depending upon the intended use of endoscope 10, 10', one or more additional elements may be provided within flexible shaft 12, 12'. For example, flexible shaft 12, 12' may include a fiber optic image bundle 24, a fiber optic illumination bundle 26, a working channel 28, etc. as is known in the art.

The control wires 20a, 20b extend from the actuator (not shown) through the flexible shaft 12, 12' to the distal end 30 of active deflection section 14, 14' where the control wires 20a, 20b are operatively connected thereto.

In some embodiments, such as the embodiment shown in FIG. 1, the active deflection section 14 is comprised of a sequence of pivotably connected rigid elements or articulating vertebrae 18. Each articulating vertebrae 18 is connected to the adjoining articulating vertebrae 18 in sequence by a joint 32, such as a pin or a resiliently deflectable element. This enables each articulating vertebrae 18 to rotate about at least one rotational degree of freedom provided by the joint 32. The combined action of the articulating vertebrae 18 allows the active deflection section 14 to be deflected 180° or more. The deflection of the active deflection section 14 is controlled by the pair of control wires 20a, 20b of the control system. Each control wire 20a, 20b passes through the articulating vertebrae 18 and connects to the distal end 30 along axes A, B eccentric to the axis C along which the joints 32 are arranged. Hence, by pulling one of the control wires 20a, 20b and releasing the other, as when operating the actuator, the articulating vertebrae 18 are rotated to achieve the requisite deflection of the active deflection section 14 of the flexible shaft 12. Various types of rigid elements or articulating vertebrae and joints linking the elements to form an active deflection section are known in the art, and therefore, the active deflection section is not described further.

In other embodiments, such as the embodiment shown in FIG. 2, the active deflection section 14' is comprised simply of a generally continuous and flexible tubular body 34. Although this configuration generally does not allow deflection to the same extent as the embodiment shown in FIG. 1, deflection is allowed to some extent. Moreover, this design, being much simpler, is typically lower is cost and easier to sterilize after use. As is the case with the embodiment shown in FIG. 1, the deflection of the active deflection section 14' is controlled by the pair of control wires 20a, 20b of the control system. Each control wire 20a, 20b passes through the tubular body 34 to the distal end 30 along axes A, B eccentric to the axis C' of tubular body 34. Hence, by pulling one of the control wires 20a, 20b and releasing the other, as when operating the actuator, the tubular body 34 is flexed to achieve the requisite deflection of the active deflection section 14' of the flexible shaft 12'. Various configurations and materials used to form an active deflection section of this type are known in the art, and therefore, the active deflection section is not described further.

The active deflection section 14, 14' is supported from the passive deflection section 16 of the flexible shaft 12, 12'. As best seen in FIG. 3, the shaft 12, 12' comprises an outer flexible casing 36, which outer flexible casing 36 covers substantially the entire flexible shaft 12, 12' from the handle to the active deflection section 14, 14'. The outer flexible casing 36 may be made from a closed wound spiral spring with an elastomer cover, a generally continuous tube (such as formed from a polymeric material or superelastic metal alloy) or any other flexible casing. Within the outer flexible casing 36, the shaft 12, 12' has an elastomeric core 38 with the control wire guides 22a, 22b extending therethrough.

Each control wire 20a, 20b passes through the shaft 12, 12' within a corresponding control wire guide 22a, 22b. Each control wire guide 22a, 22b, has a generally cylindrical tube shape. The proximal end of each control wire guide 22a, 22b is fixedly connected adjacent to the handle, while the distal end of each control wire guide 22a, 22b is fixedly connected adjacent to distal end 30 of active deflection section 14, 14'. The respective control wire guides 22a, 22b may be connected to the handle and active deflection section by any suitable means, such as adhesive, capable of transferring forces created by flexing of flexible shaft 12, 12'. In the illustrated embodiments, the control wire guides 22a, 22b, have a substantially straight natural shape. In alternate embodiments, the control wire guides may have any other longitudinal shape.

As best seen in FIGS. 4-7, the control wire guides 22a, 22b, are formed as helical springs. The springs may have any of numerous configurations. In the embodiment shown in FIGS. 4 and 5 the helical springs forming control wire guides 22a, 22b are generally round springs formed from a coiled piece of material having a generally circular cross-section, as is the case with typical helical springs. In the embodiment shown in FIGS. 6 and 7, the helical springs forming control wire guides 22a, 22b are generally flat wire springs formed from a coiled piece of material having a generally rectangular cross-section. It should be understood that springs having other configurations may also be used to form control wire guides 22a, 22b.

The springs used to form control wire guides 22a, 22b are formed from a superelastic metal alloy material, such as a nickel-titanium alloy (also known as Nitinol), which exhibits both shape memory and superelasticity properties. The superelastic metal alloy material is used for its superelastic properties exhibited by the material's ability to deflect and resiliently return to its natural or predetermined position even when material strains are high.

Forming control wire guides 22a, 22b from a superelastic metal alloy material avoids many of the problems which exists when stainless steel coil wire guides are used. One of such problems which is largely avoided is the expansion of the coil shape during compression, which can result in a loss of deflection at the active deflection section of the endoscope By using superelastic metal alloy material, little or no expansion of the control wire guides 22a, 22b takes place during compression. Forming control wire guides 22a, 22b from superelastic metal alloy material provides numerous other advantages over stainless steel coil wire guides, such as adding stiffness and/or column strength to the endoscope shaft, reducing loss of deflection over time, and improving endoscope shaft rigidity for facilitated patient introduction.

Forming the superelastic metal alloy control wire guides 22a, 22b as helical springs, rather than employing continuous-walled tubes (whether formed from stainless steel or shape memory material) reduces the likelihood of kinking, provides excellent resilience, and reduces the likelihood of permanent deformation caused by fatigue. As such, endoscopes 10, 10' of the present invention can be used effectively in applications which have a small bend radius and enjoy a longer working life as compared to endoscopes having control wire guides or sheaths formed from a continuous-walled tube.

The present invention, therefore, provides a control wire guide for use in a flexible endoscope the use of which does not result in a loss of deflection at the active deflection section of the endoscope, which adds stiffness and/or column strength to the endoscope shaft, which causes a reduction in loss of deflection over time as compared to known designs, which improves endoscope shaft rigidity for facilitated patient introduction, which can be used effectively in applications which have a small bend radius, which does not kink very easily, which has high resilience, and which does not fatigue and permanently deform thereby shortening the working life of the endoscope.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A medical device comprising:
    a flexible shaft having a proximal end and a distal end, said flexible shaft comprising an active deflection section toward the distal end;
    at least one pull control wire having a first end and a second end, said pull control wire extending from the proximal end and passing through at least a portion of said flexible shaft to the active deflection section, wherein actuation of said at least one pull control wire causes deflection of the active deflection section of said flexible shaft; and
    said at least one pull control wire being axially displaceable along a length of said flexible shaft during actuation such that a force applied to the first end is transferred to the second end;
    at least one control wire guide formed of a superelastic metal alloy surrounding said at least one pull control wire along at least a portion of a length thereof, said at least one superelastic metal alloy control wire guide configured as a helical spring providing high resilience and column strength to the flexible shaft, wherein the pull control wire allows the active deflection section to deflect without causing a loss of deflection over time due to repeated use
        wherein the superelastic metal alloy from which said at least one control wire guide is formed exhibits both shape memory and superelasticity properties.

2. The medical device of claim 1 wherein said at least one control wire guide is configured as a generally round spring formed from a coiled piece of material having a generally circular cross-section.

3. The medical device of claim 1 wherein said at least one control wire guide is configured as a generally flat wire spring formed from a coiled piece of material having a generally rectangular cross-section.

4. The medical device of claim 1 wherein the superelastic metal alloy from which said at least one control wire guide is formed comprises a nickel-titanium alloy.

5. The medical device of claim 1 wherein said at least one pull control wire comprises two pull control wires and wherein said at least one control wire guide comprises two control wire guides.

6. The medical device of claim 1 wherein said flexible shaft is generally round in cross-section.

7. The medical device of claim 1 wherein the active deflection section of said flexible shaft comprises a plurality of vertebrae pivotably connected together.

8. The medical device of claim 1 wherein the active deflection section of said flexible shaft comprises a generally continuous and flexible tubular body.

9. The medical device of claim 1 wherein said flexible shaft further comprises a passive deflection section.

10. The medical device of claim 1 wherein said flexible shaft further comprises an elastomeric core through which said at least one control wire guide extends.

11. The medical device of claim 1 wherein said flexible shaft further comprises an outer flexible casing.

12. The medical device of claim 1 further comprising a fiber optic image bundle passing through said flexible shaft.

13. The medical device of claim 1 further comprising a fiber optic illumination bundle passing through said flexible shaft.

14. The medical device of claim 1 further comprising a working channel passing through said flexible shaft.

15. The medical device of claim 1 wherein said medical device comprises an endoscope.

16. An endoscope comprising:
    a flexible shaft having a proximal end and a distal end, said flexible shaft comprising an active deflection section toward the distal end formed from a plurality of vertebrae pivotably connected together;
    two pull control wires having first and second ends, said two pull control wires extending from the proximal end and passing through at least a portion of said flexible shaft to the active deflection section, wherein actuation of said pull control wires causes the formation of a small bend radius and deflection of at least 180 degrees of the active deflection section of said flexible shaft;
    said two pull control wires being axially displaceable along a length of said flexible shaft during actuation such that a force applied to the first end of one of the two pull control wires is transferred to the second end of the pull control wire; and
    at least two control wire guides formed of a superelastic metal alloy surrounding each of said pull control wires respectively along at least a portion of a length thereof, said superelastic metal alloy control wire guides being configured as helical springs which exhibit both shape memory and superelasticity properties in order to provide high resilience while adding column strength to the flexible shaft and while facilitating deflection without causing a loss of deflection over time due.

17. The endoscope of claim 16 wherein said control wire guides are configured as generally round springs formed from coiled pieces of material having a generally circular cross-section.

18. The endoscope of claim 16 wherein said control wire guides are configured as generally flat wire springs formed from coiled pieces of material having a generally rectangular cross-section.

19. The endoscope of claim 16 wherein the superelastic metal alloy from which said control wire guides are formed comprises a nickel-titanium alloy.

20. The endoscope of claim 16 wherein said flexible shaft is generally round in cross-section.

21. The endoscope of claim 16 wherein said flexible shaft further comprises a passive deflection section.

22. The endoscope of claim 16 wherein said flexible shaft further comprises an elastomeric core through which said control wire guides extend.

23. The endoscope of claim 16 wherein said flexible shaft further comprises an outer flexible casing.

24. The endoscope of claim 16 further comprising a fiber optic image bundle passing through said flexible shaft.

25. The endoscope of claim 16 further comprising a fiber optic illumination bundle passing through said flexible shaft.

26. The endoscope of claim 16 further comprising a working channel passing through said flexible shaft.

\* \* \* \* \*